United States Patent [19]

Antranikian et al.

[11] Patent Number: 5,643,777
[45] Date of Patent: Jul. 1, 1997

[54] THERMOSTABLE PROTEASE FROM THERMOCOCCUS

[75] Inventors: Garabed Antranikian, Seevetal 1-Hittfeld; Michael Klingeberg, Gronau, both of Germany

[73] Assignee: Novo Nordisk A/S, Bagsvaerd, Denmark

[21] Appl. No.: 401,666

[22] Filed: Mar. 9, 1995

Related U.S. Application Data

[63] Continuation of Ser. No. 949,490, filed as PCT/DK91/00160, published as WO Jun. 14, 1991, abandoned.

[30] Foreign Application Priority Data

Jun. 15, 1990 [DK] Denmark .................. 1458/90

[51] Int. Cl.$^6$ ................. C12N 9/52; C11D 3/386
[52] U.S. Cl. ............... 435/220; 435/219; 435/264; 435/814; 510/114; 510/300; 510/320; 510/530
[58] Field of Search ............... 435/212, 220, 435/252.1, 219, 814, 264, 262; 424/94.64; 252/174.12

[56] References Cited

U.S. PATENT DOCUMENTS

| | | | |
|---|---|---|---|
| 3,796,635 | 3/1974 | Delente | 195/65 |
| 4,106,991 | 8/1978 | Markussen et al. | 195/63 |
| 4,480,036 | 10/1984 | Morgan et al. | 435/220 |
| 5,091,364 | 2/1992 | Baumgarten et al. | 514/8 |
| 5,242,817 | 9/1993 | Kelly et al. | 425/220 |
| 5,246,849 | 9/1993 | Bryan et al. | 435/220 |
| 5,278,062 | 1/1994 | Samal et al. | 435/223 |

FOREIGN PATENT DOCUMENTS

WO90/10072  9/1990  WIPO.

OTHER PUBLICATIONS

*The Proharyates* 2nd Edition, Barlows et al (eds). Spranger-Verlag, NYC. 1992 pp. 702–706.
Cowan et al., Chem. Abs. No. 33917f, vol. 108, No. 5, p. 278 (1987).
Zamost et al., Chem. Abs. No. 117332y, vol. 114, No. 13, p. 308 (1990).
Takii et al., Chem. Abs. No. 127292a, vol. 108, No. 15, p. 332 (1987).
Meito Sangyo Co., Ltd., Chem. Abs. No. 2625z, vol. 82, No. 1, p. 244 (1974).
Inoue et al., Chem. Abs. No. 6098r, vol. 112, No. 1, p. 18 (1990).
Tosh Corp., Patent Abs. of JP No. C551, vol. 12, No. 472 (1988).

*Primary Examiner*—Leslie Wong
*Attorney, Agent, or Firm*—Steve T. Zelson, Esq.; Valeta A. Gregg, Esq.

[57] ABSTRACT

This invention is within the field of thermostable proteases. More specifically, the present invention relates to a thermostable protease from Thermococcus celer, Thermococcus stetteri or Thermococcus litoralis, to a process for the preparation of these enzymes, and to detergent compositions comprising these enzymes. The enzyme has a temperature optimum in the range of from 75° to 100° C. and a pH optimum in the range of from 6.0–10.

10 Claims, 4 Drawing Sheets

THERMOSTABLE PROTEASE FROM THERMOCOCCUS

CROSS-REFERENCE TO RELATED APPLICATION

This application is a continuation of application Ser. No. 07/949,490 filed Oct. 22, 1992, now abandoned; which is a continuation of PCT/KD91/00160 filed Jun. 14, 1991, the contents of which are incorporated herein by reference.

TECHNICAL FIELD

This invention is within the field of thermostable proteases. More specifically, the present invention relates to novel thermostable proteases, a process for the preparation of these enzymes, and detergent compositions comprising these enzymes.

BACKGROUND ART

Hyperthermophilic archaebacteria have been isolated from solfataric and submarine hydrothermal systems (vide e.g. Kelly, R. M. & Deming, J. W.; Biotech. Progress, 4, 47–62 (1988)). It has been presumed that members of Thermococcus contain heat stable proteases and amylases (Stetter, K. O.; J. Chem. Technol. Biotechnol., 42(4), 315–317 (1988)). However, proteases from Thermococcus have not formerly been isolated or investigated.

SUMMARY OF THE INVENTION

Within the scope of the present invention novel enzymes that show extraordinary thermostability as well as thermoactivity are provided. Accordingly, in its first aspect, the present invention provides a protease that is characterized by having pH optimum in the range 6.0 to 10.0, and temperature optimum in the range 75° to 100° C. In another aspect the present invention provides a protease that is characterized by having pH optimum in the range 6.0 to 10.0, temperature optimum in the range 75° to 100° C., and immunochemical properties identical or partially identical to those of the protease derived from *Thermococcus celer*, DSM No. 2476; Thermococcus sp. AN1, DSM No. 2770; *Thermococcus stetteri*, DSM No. 5262; or *Thermococcus litoralis*, DSM No. 5474.

In yet another aspect, the present invention provides a process for the preparation of these proteases, which process comprises cultivation of a protease producing strain of Thermococcus in a suitable nutrient medium, containing carbon and nitrogen sources and inorganic salts, followed by recovery of the desired enzyme.

In preferred embodiments of this process, a strain of *Thermococcus celer*; a strain of Thermococcus sp. AN1; a strain of *Thermococcus stetteri*; or a strain of *Thermococcus litoralis*, is cultivated.

In further preferred embodiments of this process *Thermococcus celer*, DSM No. 2476; Thermococcus sp. AN1, DSM No. 2770; *Thermococcus stetteri*, DSM No. 5262; or *Thermococcus litoralis*, DSM No. 5474; or mutants or variants thereof, is cultivated.

BRIEF DESCRIPTION OF DRAWINGS

The present invention is further illustrated by reference to the accompanying drawings, wherein.

DETAILED DISCLOSURE OF THE INVENTION

Growth experiments with Thermococcus have now shown that these organisms secrete extremely thermostable and thermoactive protein hydrolysing enzymes. These enzymes possess proteolytic activity under extreme conditions. The properties of Thermococcus are demonstrated by *Thermococcus celer*, Thermococcus sp. AN1, *Thermococcus stetteri*, and *Thermococcus litoralis*. A strain of *Thermococcus celer* is available from DSM, No. 2576, a strain of Thermococcus sp. AN1 is available from DSM, No. 2770, a strain of *Thermococcus stetteri* is available from DSM, No. 5262, and a strain of *Thermococcus itoralis* is available from DSM, No. 5474.

As appears from the figures, the proteases obtainable from Thermococcus can be characterized by a pH optimum in the range of from 6.0 to 10.0, and a temperature optimum in the range of from 75° to 100° C.

Further, it appears from FIG. 1 that the protease obtainable from *Thermococcus celer* is active in a broad temperature range, namely at temperatures of from below 75° C. to above 110° C., and in a pH range of from below 5.5 to 10.5. The temperature optimum is between 90° and 100° C., more specifically around 95° C. 60% enzymatic activity are detected at 75° C., and 40% enzymatic activity are detected at 110° C. The enzyme has a pH optimum in the range of from 6.5 to 8.5, more specifically of from 7.0 to 8.0 (around 7.5). Considerable enzyme activity is still detected at pH 5.5 and 10.0, respectively.

Figure 2:
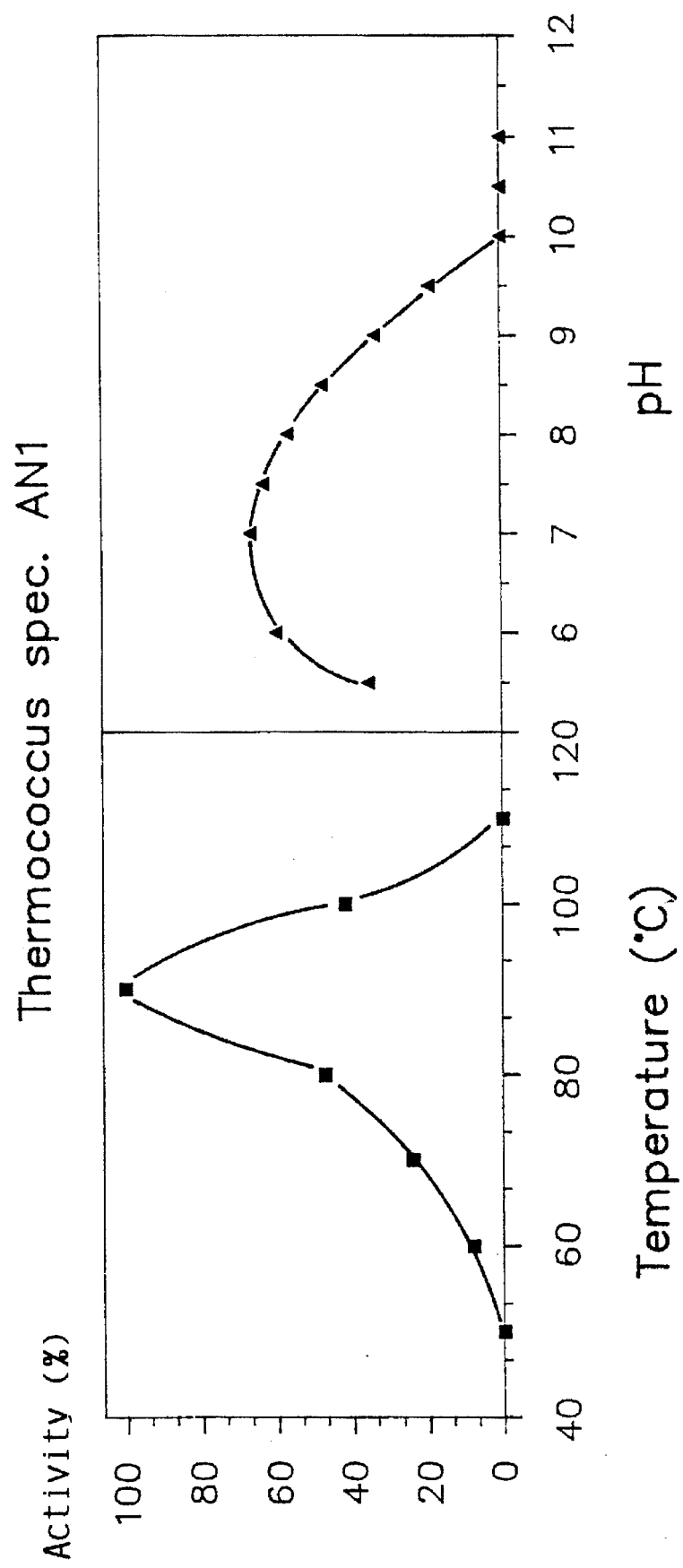
FIG. 2 shows the relation between the enzymatic activity of a protease obtained from Thermococcus sp. AN1 and temperature (at a pH of 7.0) and pH (at a temperature of 80° C.)

From FIG. 2 it appears that the protease obtainable from Thenococcus sp. AN1 is active in a temperature range of from 50° to 110° C., and in a pH range of from below 5.5 to 10. The protease has a temperature optimum in the range of from 80° to 100° C., more specifically around 90° C., and a pH optimum in the range of from 6.0 to 8.0, more specifically around 7.0.

From FIG. 3 it appears that the protease obtainable from *Thermococcus stetteri* is active in a temperature range of from below 45° C. to 100° C., and in a pH range of from below 5.5 to above 10. The protease has a temperature optimum in the range of from 75° to 85° C., more specifically around 80° C., and a pH optimum in the range of from pH 8 to 10, more specifically around pH 9.0.

From FIG. 4 it appears that the protease obtainable from *Thermococcus litoralis* is active in a temperature range of from below 60° C. to above 100° C., and in a pH range of from below 6.5 to above 11. The protease has a temperature optimum in the range of from 90° to 100° C., more specifically around 95° C., and a pH optimum in the range of from pH 8 to 10, more specifically around pH 9.0.

In table 1 some properties of the proteases from Thermococcus sp. are shown.

TABLE 1

|  | T. celer | T. AN 1 | T. stett. | T. litor. |
|---|---|---|---|---|
| pH optimum | 7.5 | 7.0 | 9.0 | 9.0 |
| temperature optimum | 95 | 90 | 80 | 95 |
| type | serine | serine | serine | serine |
| substrate specificity: | | | | |
| Z—DL—Arg—pNA | − | + | + | + |
| Suc—Ala—Ala—Pro—Phe—pNA | + | + | + | + |
| Z—DL—Lys—pNA | − | − | + | + |
| Z—Gly—Pro—pNA | − | + | − | + |
| D—Phe—Pip—Arg—pNA | + | + | + | + |
| D—Val—L—Leu—Lys—pNA | + | − | + | − |

Suc = Succinyl
pNA = p-nitroanilide
Pip = piperazine

The immunochemical properties can be determined immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publication (1983), chapters 5 and 14. The terms "antigenic identity" and "partial antigenic identity" are described in the same book, chapters 5, 19 and 20.

Preparation of the proteases

The proteases according to the present invention can be prepared by cultivation of a protease producing strain of Thermococcus in a suitable nutrient medium, containing carbon and nitrogen sources and inorganic salts, followed by recovery of the desired enzyme, by methods known in the art.

The protease according to the present invention can also be prepared by recombinant DNA-technology.

Detergent compositions

Due to the unique properties of the proteases according to the present invention, these enzymes are of great interest for industrial applications, e.g. for use in the detergent industry.

The detergent composition of the invention may comprise one or more surfactants, which may be of an anionic, non-ionic, cationic amphoteric or zwitter-ionic type, or a mixture of these. Typical examples of anionic surfactants are linear alkyl benzene sulfonates (LAS); alkyl sulfates (AS); alpha olefin sulfonates (AOS); alcohol ethoxy sulfates (AES) and alkali metal salts of natural fatty acids. Examples of non-ionic surfactants are alkyl polyethylene glycol ethers; nonylphenol polyethylene glycol ethers; fatty acids esters of sucrose and glucose; and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in J. Falbe [Falbe, J.; Surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form, such as powders, liquids, etc.

The detergent composition of the invention may advantageously include one or more other enzymes, e.g. lipases; amylases; cellulases; and/or peroxidases, conventionally included in detergent compositions.

The protease of the invention may be included in a detergent composition by adding separate additives containing the detergent protease, or by adding a combined additive comprising different detergent enzymes.

The additive of the invention can be formulated e.g. as granulates, liquids, slurries, etc. Preferred detergent additive formulations are non-dusting granulates, liquids, in particular stabilized liquids, slurries, or protected enzymes. Dust free granulates may be produced according to e.g. GB 1,362,365 or U.S. 4,106,991, and may optionally be coated by methods known in the art. The detergent enzymes may be mixed before or after granulation. Liquid enzyme preparations may, for instance, be stabilized by adding a polyol such as e.g. propylene glycol; a sugar or sugar alcohol; lactic acid or boric acid, according to established methods. Other enzyme stabilizers are well known in the art. Protected enzymes may be prepared according to the method disclosed in U.S. No. 4,906,396

The following examples further illustrate the present invention.

EXAMPLE 1

Cultivation of *Thermococcus celer*

*Thermococcus celer*, DSM No. 2476, was cultivated in a nutrient medium containing the following components (per 1 liter):

| | |
|---|---|
| NaCl | 40.00 g |
| $(NH_4)_2SO_4$ | 1.30 g |
| $KH_2PO_4$ | 0.28 g |
| $MgSO_4.7H_2O$ | 0.25 g |
| $CaCl_2.2H_2O$ | 0.07 g |
| $FeCl_3.6H_2O$ | 2.000 mg |
| $MnCl_2.4H_2O$ | 1.800 mg |
| $Na_2B_4O_7.10H_2O$ | 4.500 mg |
| $ZnSO_4.7H_2O$ | 0.220 mg |
| $CuCl_2.2H_2O$ | 0.050 mg |
| $Na_2MoO_4.2H_2O$ | 0.030 mg |
| $VOSO_4.5H_2O$ | 0.038 mg |
| $CoSO_4$ | 0.010 mg |
| Yeast extract | 1.00 g |
| Peptone | 1.00 g |
| Resazurin | 1.000 mg |
| Sulphur (powdered) | 5.00 g |
| $Na_2S.9H_2O$ | 0.50 g |
| Adjust pH to pH 5.8 | |

The medium without sodium sulphide and sulphur was boiled for 20 minutes, cooled on ice and dispensed under $N_2$ atmosphere. The medium was then filled under $N_2$ atmosphere into 100 ml vials containing sulphur. For sterilization the medium was heated to 1000° C. for 1 hour on each of 3 successive days.

Before inoculation the medium was reduced by adding 10 ml/l of sterile neutral sodium sulphide (5% solution). The medium was inoculated with 10% of a grown preculture and finally incubated at 88° C. for 24–36 hours.

Assay for proteolytic activity

The enzymatic reaction was conducted in a 50 mM of phosphate buffer, pH 7.0, containing 0.25% of casein (Hammarsten, Serva, Heidelberg, FRG). The reaction was initiated by the addition of 250 µl of cell suspension to 2250

µl assay mixture. Samples (500 µl each) were taken after incubation at 90° C. for 30, 60, 90, and 120 min. The reaction was stopped by cooling the samples on ice and by the addition of 500 µl of trichloroacetic acid (10% solution). The mixture was allowed to stand at room temperature for 30 min. and then centrifuged for 10 min. at 12000 rpm. The absorbance of the supernatant was measured at 280 nm against a blank. 1 U of enzyme is defined as the amount of enzyme which liberates 1µmol of tyrosine per min.

Characterization of the protease

In order to study the effect of pH and temperature on enzyme activity a buffer mixture which was composed of 20 mM MES (2-[N-Morpholino]ethanesulfonic acid), 20 mM HEPES (N-2- hydroxyethylpiperazine-N'-2-ethanesulfonic acid) and 20 mM Glycine was used. The pH value was varied from 5.5 to 11.0 in increments of 0.5, and the temperature was varied from 75 to 110° C. Casein (0.25%) was used as a substrate.

Figure 1:
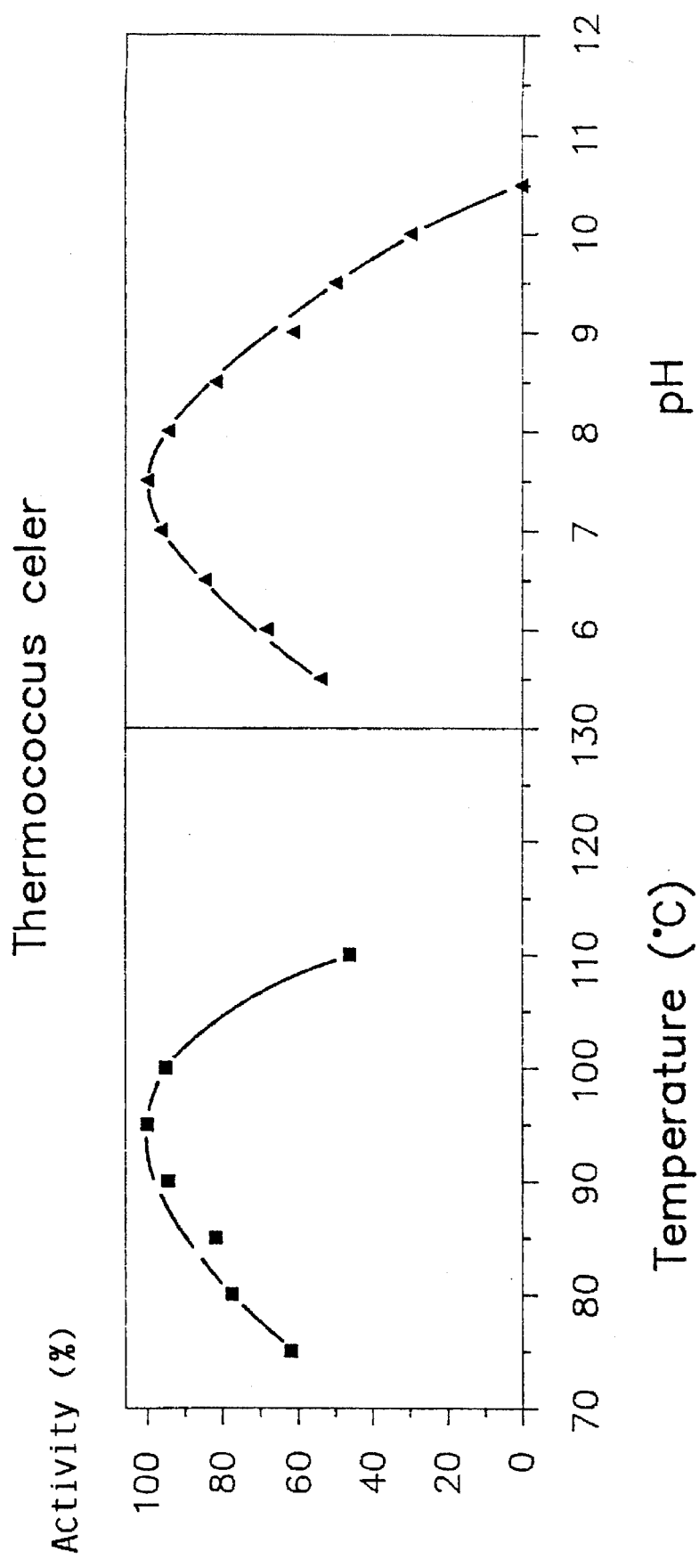
FIG. 1 shows the relation between the enzymatic activity of a protease obtained from *Thermococcus celer* and temperature (at a pH of 7.0) and pH (at a temperature of 90° C.)

As shown in FIG. 1, the protease from *T. celer* was active in a broad temperature and pH range. 60% and 40% of enzyme activity was still detected at 75° C. and 110° C., respectively; the temperature optimum being 90° to 1000° C. The enzyme had a pH optimum of around 7.5, and considerable activity was also detected at pH 5 and 10.

EXAMPLE 2

Cultivation of Thermococcus sp. AN1

Thermococcus sp. AN1, DSM No. 2770, was cultivated in a nutrient medium containing the following components (per liter):

| | |
|---|---|
| Trypticase (BBL) | 10.0 g |
| $KH_2PO_4$ | 1.5 g |
| NaCl | 2.5 g |
| Sulphur (powdered) | 8.0 g |
| $Na_2S.9H_2O$ | 0.5 g |
| Resazurin | 1.0 mg |
| Adjust pH to 7.3 | |

The medium without sodium sulphide and sulphur was boiled for 20 minutes, cooled on ice and dispensed under $N_2$ atmosphere. The medium was then filled into a 100-ml vial containing sulphur under $N_2$ atmosphere. For sterilization the medium was heated to 100° C. for 1 hour on each of 3 successive days.

Before inoculation with 10% of a grown preculture the medium was reduced by adding 10 ml/l of sterile neutral sodium sulphide (5% solution). Bacteria were cultivated at 75° C. for 24–36 hours.

Assay for proteolytic activity

The enzymatic reaction was conducted in 50 mM of phosphate buffer, pH 7.0, containing 0.25% of casein (Hammarsten Serva, Heidelberg, FRG). The reaction was initiated by the addition of 250 µl of cell suspension to 2250 µl assay mixture. Samples (500 µl each) were taken after incubation at 80° C. for 30, 60, 90, and 120 min. The reaction was stopped by cooling the samples on ice and by the addition of 500 µl of trichloroacetic acid (10% solution). The mixture was allowed to stand at room temperature for 30 min. and then centrifuged for 10 min. at 12000 rpm. 1 U of enzyme is defined as the amount of enzyme which liberates 1 µmol of tyrosine/min.

Characterization of the protease

Casein (Hammarsten) was dissolved at a concentration of 0.25% in a buffer mixture which was composed of 20 mM MES (2-[N-Morpholino]ethanesulfonic acid), 20 mM HEPES (N-2- hydroxyethylpiperazine-N'-2-ethanesulfonic acid) and 20 mM Glycine at pH-values from 5.5 to 9, and at temperatures from 50° to 110° C.

As shown in FIG. 2, the level of protease activity reached a maximum around pH 7.0. At a pH-value of 5.5 and 9.0 approximately 35% of activity could be detected. Optimum proteolytic activity for the substrate casein occurred at 90°C. Approximately 50% of enzyme activity was measured at 100° C.

EXAMPLE 3

Cultivation of *Thermococcus stetteri*

*Thermococcus stetteri*, DSM No. 5262, was cultivated in a nutrient medium containing the following components (per liter):

| | |
|---|---|
| NaCl | 25.00 g |
| $NH_4Cl$ | 0.33 g |
| $CaCl_2.2\ H_2O$ | 0.33 g |
| $MgCl_2.6\ H_2O$ | 0.33 g |
| KCl | 0.33 g |
| $KH_2PO_4$ | 0.33 g |
| Trace element solution (see DSM-medium 320) | 1.0 ml |
| Vitamin solution (see DSM-medium 320) | 10.0 ml |
| Trypticase BBL | 5.00 g |
| Sulphur powdered | 10.00 g |
| Resazurin | 1.00 mg |
| $Na_2S.9\ H_2O$ | 0.50 g |
| pH 5.7 | |

The medium without sodium sulphide and sulphur was boiled for 20 minutes, cooled on ice and dispensed under $N_2$ atmosphere. The medium was then filled into a 100-ml vial containing sulphur under $N_2$ atmosphere. For sterilization the medium was heated to 100° C. for 1 hour on each of 3 successive days.

Before inoculation with 10% of a grown preculture the medium was reduced by adding 10 ml/l of sterile neutral sodium sulphide (5% solution). Bacteria were cultivated at 800° C. for 24–36 hours.

Assay for proteolytic activity

The assay mixture contained 0.25% casein (Hammarsten) which was dissolved in 50 mM Tris/Glycine buffer, pH 9.0. The reaction was initiated by the addition of 250 µl cell suspension to 2350 µl assay mixture at 80° C. Samples (500 µl each) were taken after 30, 60, 90, 120 min. The reaction was stopped by cooling on ice and by the addition of 500 ml of trichloroacetic acid (10%). The mixture was allowed to stand at room temperature for about 30 minutes and centrifugated afterwards for 10 minutes at 12,000 r.p.m. The absorbance of the supernatant was determined at 280 nm against a blank. 1 U of enzyme is defined as that amount of enzyme which liberates 1 µmol of tyrosine per minute under the specified conditions.

Characterization of the protease

Casein (Hammarsten) was dissolved at a concentration of 0.25% in a buffer mixture which was composed of 20 mM MES (2-[N-Morpholino]ethanesulfonic acid), 20 mM HEPES (N-2-hydroxyethylpiperazine-N'-2-ethanesulfonic acid) and 20 mM Glycine at pH-values from 5.5 to 10, and at temperatures from 45° to 100° C.

Figure 3:
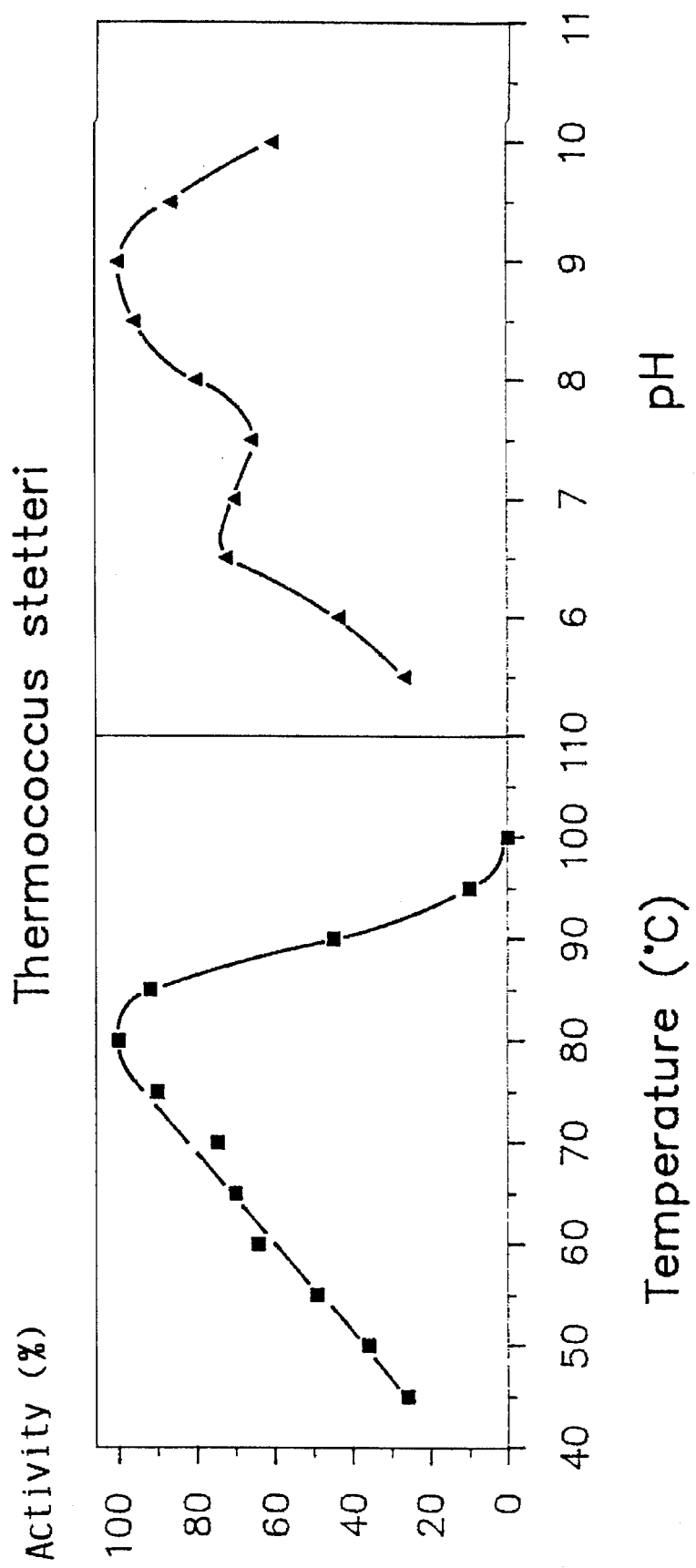
FIG. 3 shows the relation between the enzymatic activity of a protease obtained from *Thermococcus stetteri* and temperature (at a pH of 9.0) and pH (at a temperature of 80° C.)

As shown in FIG. 3, the level of protease activity reached a maximum around pH 9.0. At a pH-value of 5.5 approximately 30% of activity could be detected and at a pH-value of 10.0 approximately 70% of activity could be detected. Optimum proteolytic activity for the substrate casein occurred at 80° C. Approximately 30% of enzyme activity was measured at 45° C.

EXAMPLE 4

Cultivation of *Thermococcus litoralis*

*Thermococcus litoralis*, DSM No. 5474, was cultivated in a nutrient medium containing the following components (per liter):

| | |
|---|---|
| NaCl | 19.45 g |
| $MgCl_2.6 H_2O$ | 12.60 g |
| $Na_2SO_4$ | 3.42 g |
| $CaCl_2.2 H_2O$ | 2.38 g |
| KCl | 0.55 g |
| $Na_2CO_3$ | 0.61 g |
| KBr | 0.08 g |
| $SrCl_2$ | 57.2 mg |
| $Na_2HPO_4$ | 10.0 mg |
| Na metasilicate | 4.0 mg |
| NaF | 2.4 mg |
| $KNO_3$ | 1.6 mg |
| Resazurin | 100.0 mg |
| Yeast extract | 1.0 g |
| Bactopeptone | 5.0 g |
| Sulphur powdered | 10.0 g |
| $Na_2S.9 H_2O$ | 0.5 g |
| ad 1000 ml $H_2O$dest. pH 6.5 | |

The medium without sodium sulphide and sulphur was boiled for 20 minutes, cooled on ice and dispensed under $N_2$ atmosphere. The medium was then filled under $N_2$ atmosphere into 100-ml vials containing sulphur. For sterilization the medium was heated to 100° C. for 1 hour on each of 3 successive days.

Before inoculation the medium was reduced by adding 10 ml/l of sterile neutral sodium sulphide (5% solution). The medium was inoculated with 10% of a grown preculture and finally incubated at 85° C. for 24–36 hours.

Assay for proteolytic activity

The assay mixture contained 0.25% casein (Hammarsten) which was dissolved in 50 mM Tris/Glycine buffer, pH 9.0. The reaction was initiated by the addition of 250 µl cell suspension to 2350 µl assay mixture at 90° C. Samples (500 µl each) were taken after 30, 60, 90, 120 min. The reaction was stopped by cooling and by the addition of 500 ml of trichloroacetic acid (10%). The mixture was allowed to stand at room temperature for about 30 minutes and centrifugated afterwards for 10 minutes at 12,000 r.p.m. The absorbance of the supernatant was determined at 280 nm against a blank. 1 U of enzyme is defined as that amount of enzyme which liberates 1 µmol of tyrosine per minute under the specified conditions.

Characterization of the protease

Casein (Hammarsten) was dissolved at a concentration of 0.25% in a buffer mixture which was composed of 20 mM MES (2-[N-Morpholino]ethanesulfonic acid), 20 mM HEPES (N-2-hydroxyethylpiperazine-N'-2-ethanesulfonic acid) and 20 mM Glycine at pH-values from 6.5 to 11, and at temperatures from 60° to 100° C.

Figure 4:
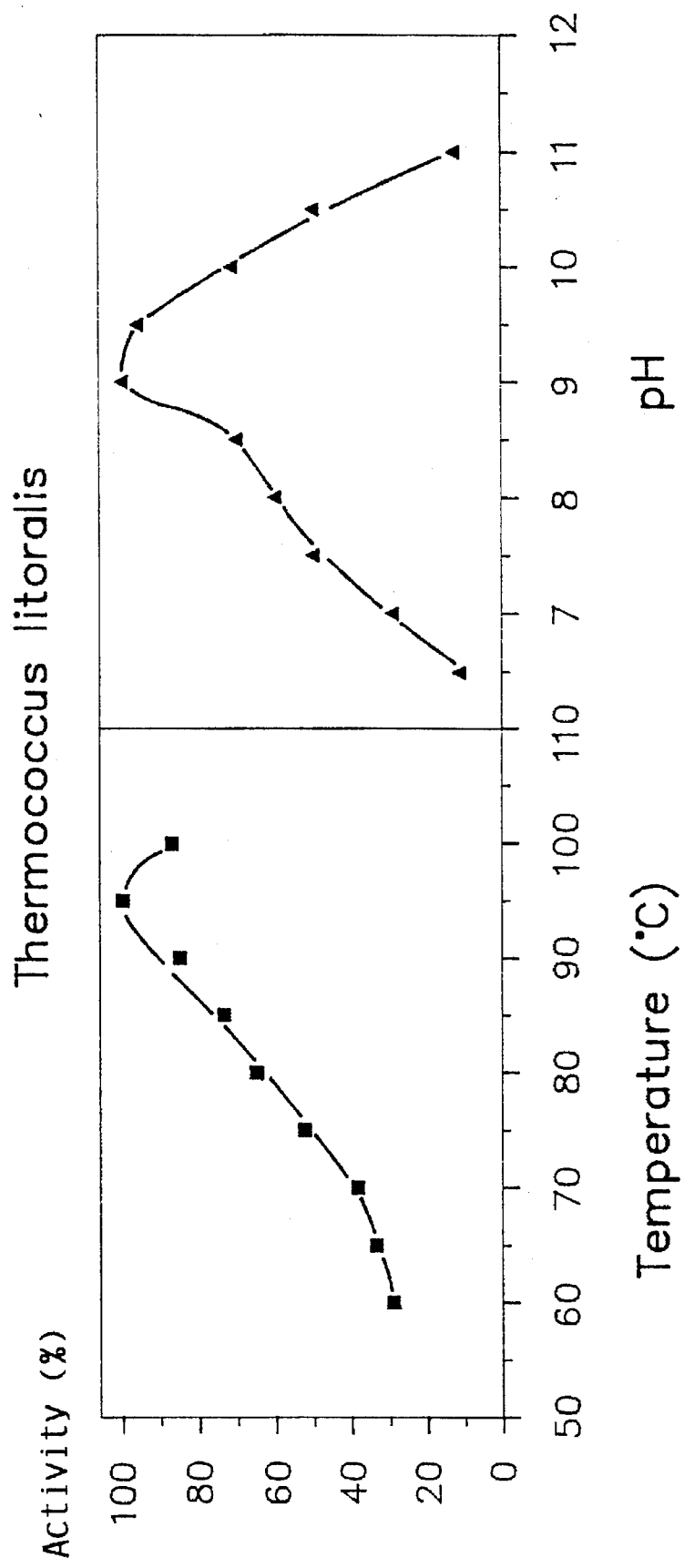
FIG. 4 shows the relation between the enzymatic activity of a protease obtained from *Thermococcus litoralis* and temperature (at a pH of 9.0) and pH (at a temperature of 90° C.).

As shown in FIG. 4, the level of protease activity reached a maximum around pH 9.0. At a pH-value of 5.5 and 11 approximately 10% of activity could be detected. Optimum proteolytic activity for the substrate casein occurred at 95° C. Approximately 90% of enzyme activity was measured at 100° C., and approximately 30% of enzyme activity was measured at 60° C.

We claim:

1. An enzyme preparation comprising an enzyme having serine protease activity, wherein the enzyme is characterized as having:

(a) a pH optimum in the range of 8.0–10.0 at a temperature of 80° C.;

(b) a temperature optimum in the range of 75°–85° C. at a pH of 9.0; and (c) is derived from a strain of *Thermococcus stetteri*.

2. The enzyme preparation according to claim 1, wherein the pH optimum is about 9.0 and the temperature optimum is about 80° C.

3. The enzyme preparation according to claim 1 wherein the strain is DSM No. 5262.

4. A detergent additive, comprising the enzyme preparation according to claim 1 in a form selected from the group consisting of a non-dusting granulate, a liquid, a slurry and a protected enzyme.

5. A detergent composition comprising the enzyme preparation according to claim 1 and a suitable surfactant.

6. An enzyme preparation comprising an enzyme having serine protease activity, wherein the enzyme is characterized as having (a) a pH optimum in the range of 8.0–10.0 at a temperature of 90° C.;

(b) a temperature optimum in the range of 90°–100° C. at a pH of 9.0; and (c) is derived from a strain of *Thermococcus litoralis*.

7. The enzyme preparation according to claim 6 wherein the pH optimum is about 9.0 and the temperature optimum is about 95° C.

8. The enzyme preparation according to claim 6, wherein the strain is DSM No. 5474.

9. A detergent additive, comprising the enzyme preparation according to claim 6 in a form selected from the group consisting of a non-dusting granulated, a liquid, a slurry and a protected enzyme.

10. A detergent composition the enzyme preparation according to claim 6 and a suitable surfactant.

* * * * *